US012290242B2

(12) United States Patent
Ohno et al.

(10) Patent No.: US 12,290,242 B2
(45) Date of Patent: May 6, 2025

(54) CAMERA HEAD

(71) Applicant: Sony Olympus Medical Solutions Inc., Tokyo (JP)

(72) Inventors: Atsuomi Ohno, Tokyo (JP); Takuya Taniguchi, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 681 days.

(21) Appl. No.: 17/134,522

(22) Filed: Dec. 28, 2020

(65) Prior Publication Data

US 2021/0251477 A1    Aug. 19, 2021

(30) Foreign Application Priority Data

Feb. 18, 2020    (JP) .................................. 2020-024943

(51) Int. Cl.
*A61B 1/00*    (2006.01)
*A61B 1/05*    (2006.01)
*A61B 1/12*    (2006.01)

(52) U.S. Cl.
CPC ............ *A61B 1/121* (2013.01); *A61B 1/0011* (2013.01); *A61B 1/00124* (2013.01); *A61B 1/00195* (2013.01); *A61B 1/053* (2013.01)

(58) Field of Classification Search
CPC ... A61B 1/121; A61B 1/0011; A61B 1/00124; A61B 1/00195; A61B 1/053; A61B 1/00128; A61B 1/00137; A61B 1/042
See application file for complete search history.

(56) References Cited

U.S. PATENT DOCUMENTS

| | | | | |
|---|---|---|---|---|
| 5,808,813 A | * | 9/1998 | Lucey | G02B 23/2438 359/823 |
| 6,080,101 A | | 6/2000 | Tatsuno | |
| 2002/0128539 A1 | * | 9/2002 | Higuma | G02B 23/2453 600/162 |
| 2006/0282048 A1 | * | 12/2006 | Kimura | A61B 17/3478 604/272 |

(Continued)

FOREIGN PATENT DOCUMENTS

| | | | |
|---|---|---|---|
| JP | 2000333903 A | | 12/2000 |
| JP | 2013056003 A | * | 3/2013 |
| JP | 2017006207 A | | 1/2017 |

(Continued)

*Primary Examiner* — Timothy J Neal
(74) *Attorney, Agent, or Firm* — XSENSUS LLP

(57) ABSTRACT

A camera head includes: a casing including an opening and configured to receive a subject image introduced inside through the opening; an image sensor housed in the casing and configured to capture the subject image; an optical element made of a translucent material and fixed to an inner circumferential surface of the opening by brazing with solder to airtightly seal inside of the casing; and a watertight sealing member fixed to the casing and watertightly sealing the solder joining the casing and the optical element, the watertight sealing member including an annular elastic portion made of an elastic material, and a pressing portion including an annular pressing surface configured to press the elastic portion toward the optical element when the elastic portion abuts on an outer surface of the optical element facing space outside the casing, the pressing portion being fixed to the casing.

20 Claims, 10 Drawing Sheets

(56) References Cited

U.S. PATENT DOCUMENTS

2018/0035878 A1\* 2/2018 Nara .................... A61B 1/0011
2019/0167374 A1\* 6/2019 Calavrezos .......... A61B 1/0014

FOREIGN PATENT DOCUMENTS

JP          6411291 B2 \* 10/2018
JP          6465439 B2 \*  2/2019
WO   WO-2017002587 A1    1/2017

\* cited by examiner

CAMERA HEAD

CROSS-REFERENCE TO RELATED APPLICATION

This application claims priority from Japanese Application No. 2020-024943, filed on Feb. 18, 2020, the contents of which are incorporated by reference herein in its entirety.

BACKGROUND

The present disclosure relates to a camera head.

In the related art, a camera head has been known. The camera head is inserted into a subject, detachably connected to an eyepiece unit of an endoscope to capture a subject image from the subject, and captures a subject image emitted from the eyepiece unit (see, for example, JP 2017-6207 A).

Incidentally, such a camera head is subjected to autoclave treatment (high-temperature and high-pressure steam sterilization treatment), or disinfection treatment by wiping or immersion before use. This means that the camera head needs to have a structure in which high-temperature and high-pressure steam used in the autoclave treatment and any chemical liquid used in the disinfection treatment by wiping or immersion do not easily penetrate inside.

In the camera head described in JP 2017-6207 A, an optical element is fixed to an inner circumferential surface of an opening in a casing unit, housing therein an image sensor, by brazing with solder to airtightly seal the inside of the casing unit.

SUMMARY

The solder may involve voids (air bubbles) and dents. In addition, it is difficult to control the surface roughness of the surface of the solder.

In the camera head described in JP 2017-6207 A, the solder joining the casing unit and the optical element is exposed to the outside of the casing unit. When the surface roughness of the surface of the solder increases, there is a risk in that dirt will remain on the surface of the solder while the camera head is being used. There is no problem with the dirt remaining on the surface when the surface roughness of the surface of the solder increases at present; however, it may be assumed that higher cleanability than the present is necessary in the future.

There is a need for a camera head capable of improving cleanability.

According to one aspect of the present disclosure, there is provided a camera head including: a casing including an opening and configured to receive a subject image introduced inside through the opening; an image sensor housed in the casing and configured to capture the subject image; an optical element made of a translucent material and fixed to an inner circumferential surface of the opening by brazing with solder to airtightly seal inside of the casing; and a watertight sealing member fixed to the casing and watertightly sealing the solder joining the casing and the optical element, the watertight sealing member including an annular elastic portion made of an elastic material, and a pressing portion including an annular pressing surface configured to press the elastic portion toward the optical element when the elastic portion abuts on an outer surface of the optical element facing space outside the casing, the pressing portion being fixed to the casing.

DETAILED DESCRIPTION

Figure 1:
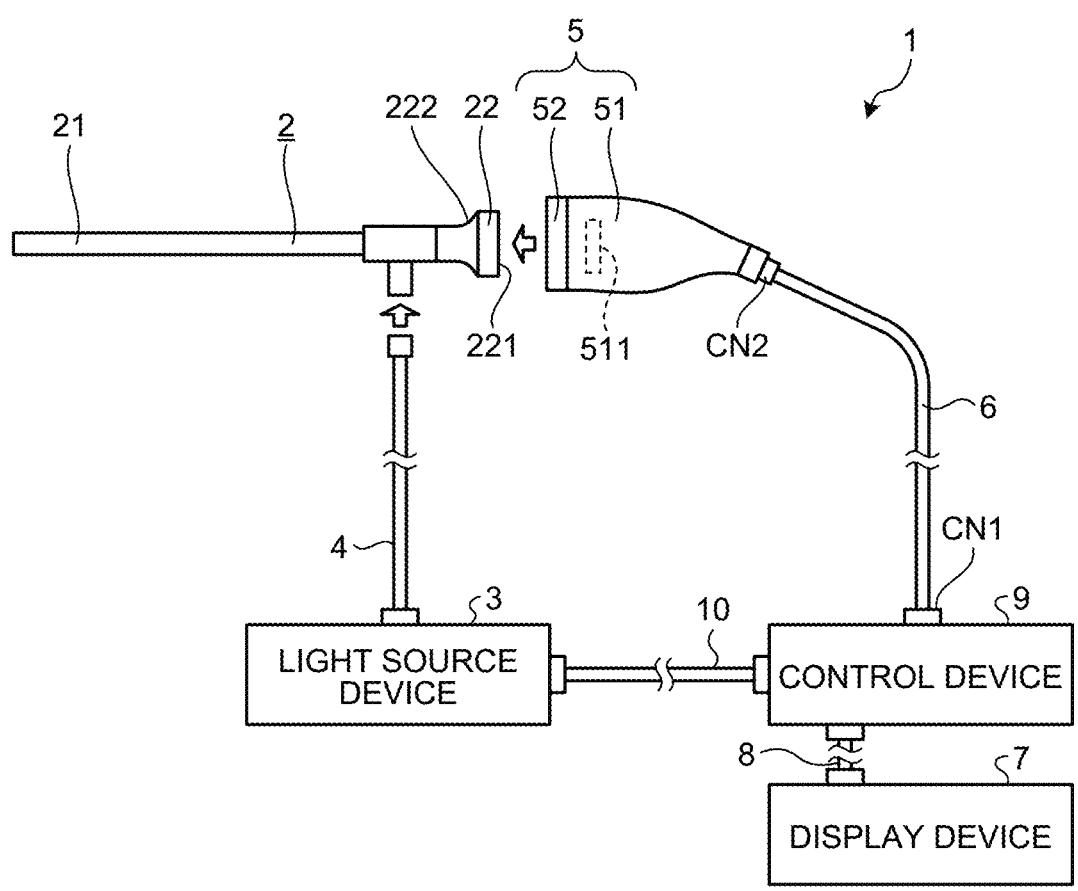
FIG. 1 is a diagram illustrating a schematic configuration of a medical observation system according to a first embodiment.

Hereinafter, modes for carrying out the present disclosure (hereinafter referred to as embodiments) will be described with reference to the drawings. The present disclosure is not limited to the embodiments described below. Furthermore, in the drawings, the same components are denoted with the same reference numerals.

First Embodiment

Schematic Configuration of Medical Observation System

FIG. 1 is a diagram illustrating a schematic configuration of a medical observation system 1 according to a first embodiment.

The medical observation system 1 is a system that is used in the medical field for observing the inside of a living body. As illustrated in FIG. 1, this medical observation system 1 includes an endoscope 2, a light source device 3, a light guide 4, a camera head 5, a first transmission cable 6, a display device 7, a second transmission cable 8, a control device 9, and a third transmission cable 10.

The endoscope 2 is a rigid endoscope. Specifically, the endoscope 2, to be inserted into a living body, has an elongated shape and is entirely rigid or is partially flexible and partially rigid. As illustrated in FIG. 1, the endoscope 2 includes an insertion unit 21 and an eyepiece unit 22.

The insertion unit 21 is a part that extends linearly to be inserted into a living body. The insertion unit 21 is provided with an optical system (not illustrated) that includes one or a plurality of lenses and focuses light for a subject image.

The eyepiece unit 22 is provided at the proximal end of the insertion unit 21. In this eyepiece unit 22, there is provided an eyepiece optical system (not illustrated) that emits a subject image focused by the optical system in the insertion unit 21 to the outside from the eyepiece unit 22.

Note that the detailed shape of the eyepiece unit 22 will be described in "Shape of eyepiece unit" described below.

The light source device 3 is connected to one end of the light guide 4 and supplies light for illuminating the living body to one end of the light guide 4 under the control of the control device 9.

Note that, in the first embodiment, the light source device 3 is formed to be separated from the control device 9. However, this should not be construed in a limiting sense, and a configuration where the light source device 3 is provided inside the control device 9 may be employed.

The light guide 4 has one end detachably connected to the light source device 3, and the other end detachably connected to the endoscope 2. The light supplied from the light source device 3 travels from one end of the light guide 4 to the other end to be supplied to the endoscope 2. The light supplied to the endoscope 2 is emitted onto the living body from the distal end of the insertion unit 21. Light (subject image) emitted into the living body and reflected in the living body is focused by the optical system in the insertion unit 21.

As illustrated in FIG. 1, the camera head 5 includes a sealed unit 51 in which an image sensor 511 and the like are airtightly housed, and an endoscope connector 52 provided in the sealed unit 51 and detachably connected to the eyepiece unit 22 of the endoscope 2. Here, the image sensor 511 is provided on an optical axis Ax (see FIG. 4) of the subject image emitted from the eyepiece unit 22 of the endoscope 2. Then, the camera head 5 captures the subject image focused by the endoscope 2 with the image sensor 511, and outputs an image signal (PAW signal) as a result of the image capturing, under the control of the control device 9. The image signal is, for example, an image signal of 4K or of a higher quality.

Note that the detailed configurations of the sealed unit 51 and the endoscope connector 52 will be respectively described in "Configuration of sealed unit" and "Configuration of endoscope connector" described below.

The first transmission cable 6 has one end detachably connected to the control device 9 via a connector CN1 (FIG. 1) and the other end detachably connected to the camera head 5 via a connector CN2 (FIG. 1). Through the first transmission cable 6, an image signal and the like output from the camera head 5 are transmitted to the control device 9, and a control signal, a synchronization signal, clock, power, and the like, output from the control device 9, are each transmitted to the camera head 5.

Note that the transmission of the image signal or the like from the camera head 5 to the control device 9 through the first transmission cable 6 may be implemented by transmitting the image signal or the like as an optical signal or as an electrical signal. The same applies to transmission of the control signal, the synchronization signals, and the clock from the control device 9 to the camera head 5 through the first transmission cable 6.

The display device 7 is formed by a display using liquid crystals, organic electro luminescence (EL), or the like, and displays an observation image based on a video signal from the control device 9 under the control of the control device 9.

The second transmission cable 8 has one end detachably connected to the display device 7, and has the other end detachably connected to the control device 9. The second transmission cable 8 transmits the video signal processed by the control device 9 to the display device 7.

The control device 9 includes a central processing unit (CPU) and the like, and comprehensively controls the operations of the light source device 3, the camera head 5, and the display device 7.

Specifically, the control device 9 generates a video signal by performing various processing on an image signal acquired from the camera head 5 through the first transmission cable 6, and outputs the video signal to the display device 7 through the second transmission cable 8. Then, the display device 7 displays an observation image based on the video signal. Furthermore, the control device 9 outputs a control signal and the like to the camera head 5 and the light source device 3 through the first and third transmission cables 6 and 10.

The third transmission cable 10 has one end detachably connected to the light source device 3, and has the other end detachably connected to the control device 9. Through the third transmission cable 10, the control signal, from the control device 9, is transmitted to the light source device 3.

Configuration of Sealed Unit

Next, the configuration of the sealed unit 51 will be described.

It should be noted that the "distal end side" described below means the distal end side of the endoscope 2 (left side in FIGS. 1 to 5). The "proximal end side" means the side away from the distal end of the endoscope 2 (right side in FIGS. 1 to 5).

Figure 2:
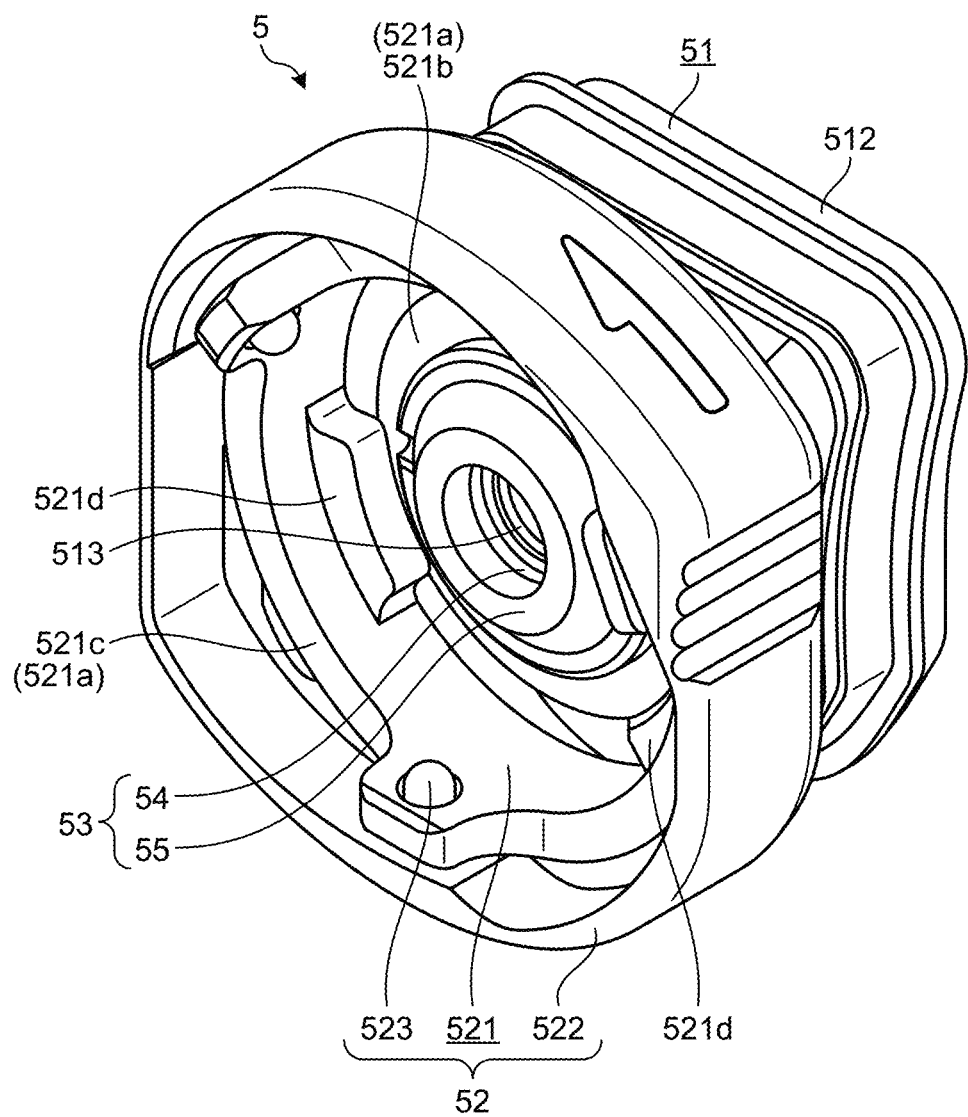
FIG. 2 is a diagram illustrating a configuration of a camera head.
Figure 3:
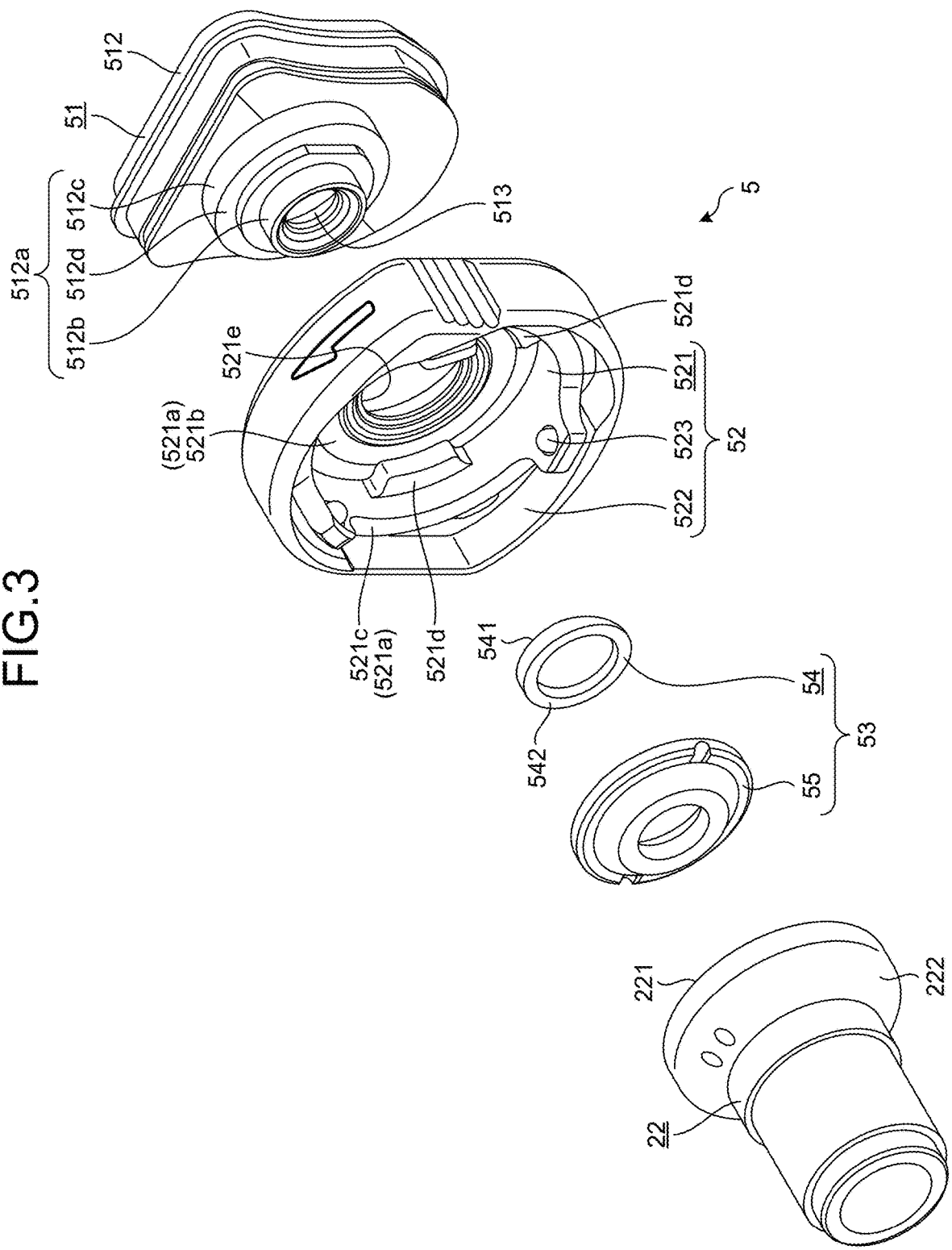
FIG. 3 is a diagram illustrating the configuration of the camera head.
Figure 4:
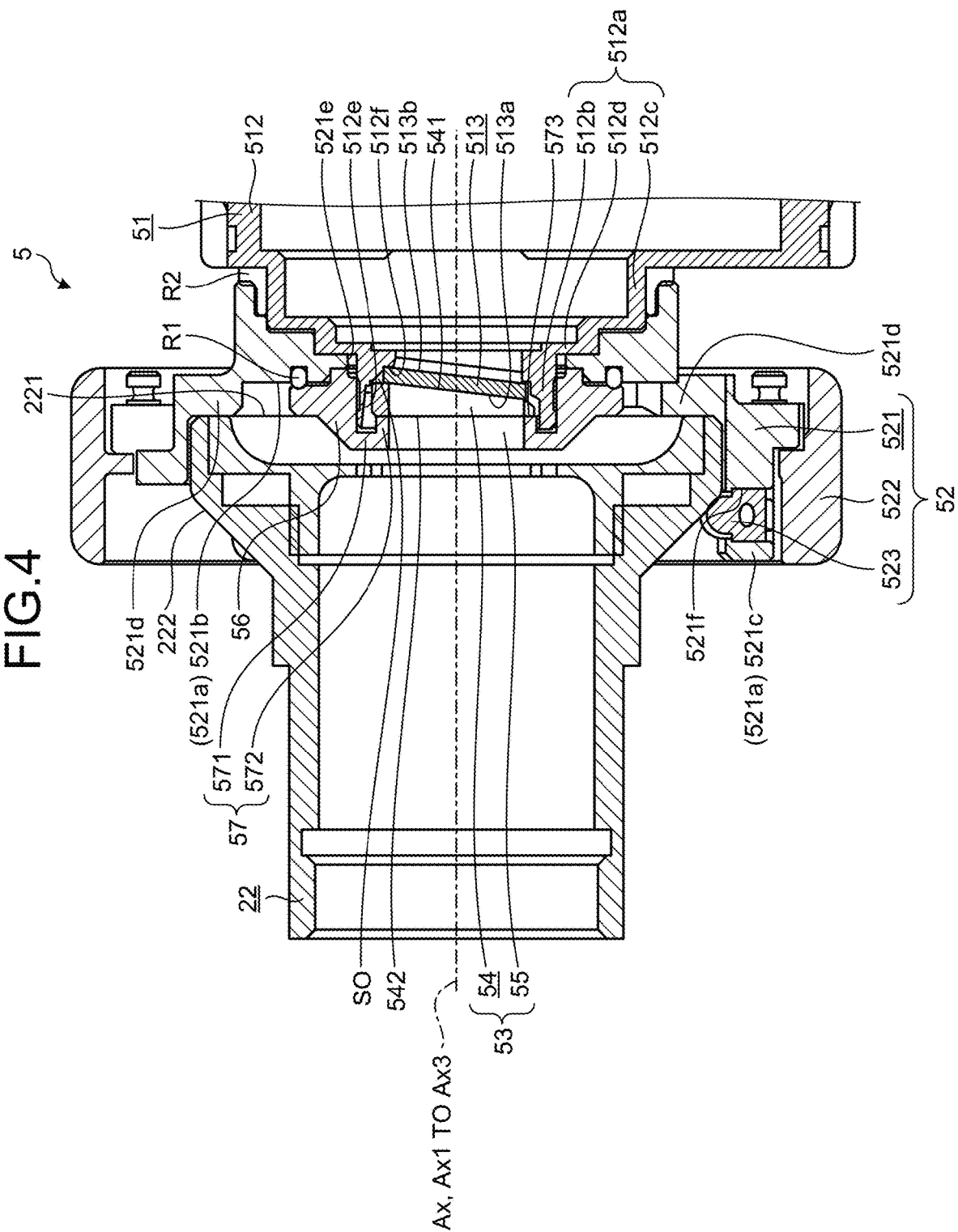
FIG. 4 is a diagram illustrating the configuration of the camera head.
Figure 5:
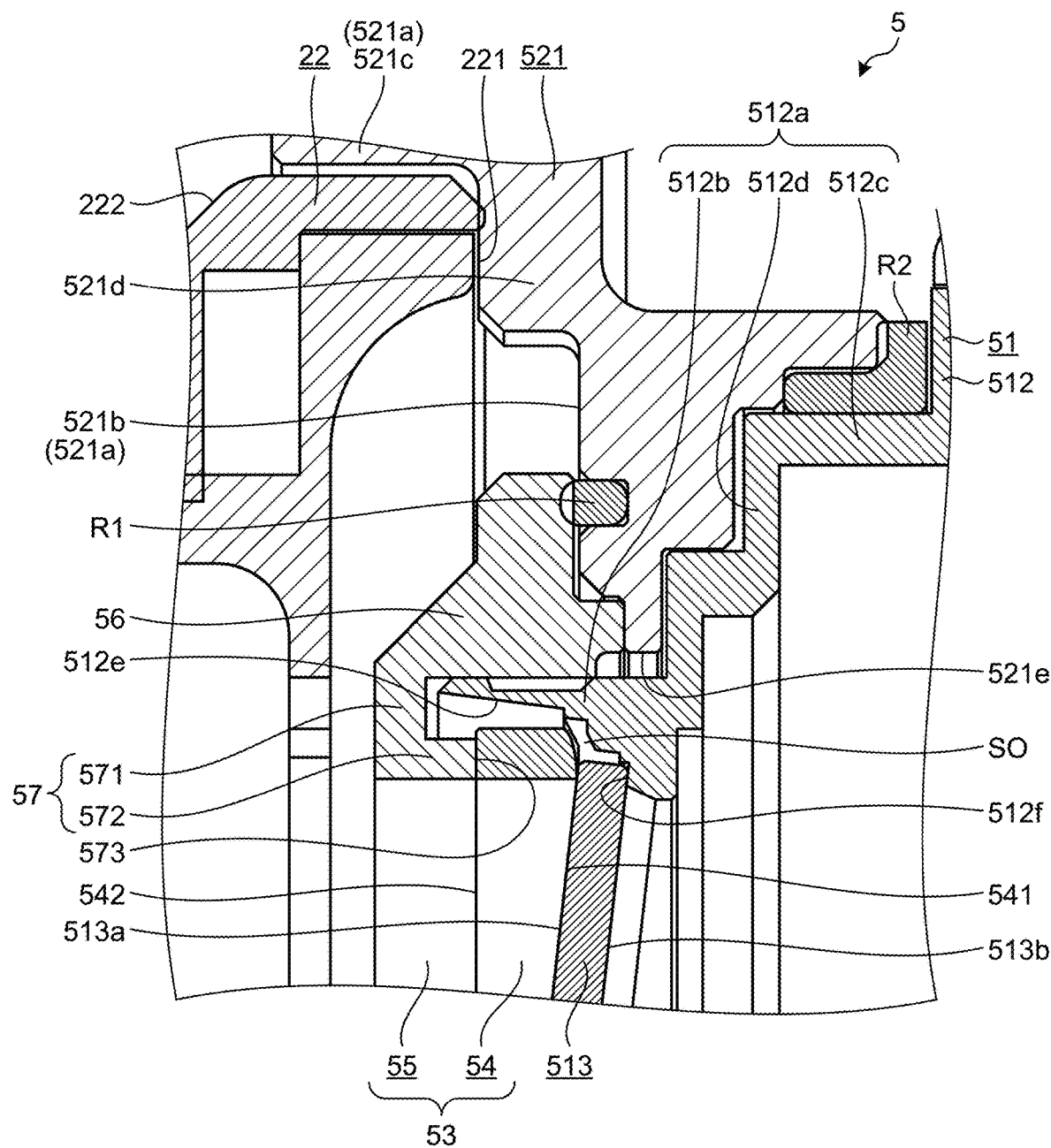
FIG. 5 is an enlarged view of a part of FIG. 4.

FIGS. 2 to 4 are diagrams illustrating the configuration of the camera head 5. Specifically, FIG. 2 is a perspective view of the camera head 5 as viewed from the distal end side. FIG. 3 is an exploded perspective view of a distal end side part of the camera head 5. FIG. 4 is a cross-sectional view of the distal end side part of the camera head 5 cut along a plane along the optical axis Ax of the subject image. In FIGS. 2 to 4, only the distal end side part is illustrated as the sealed unit 51 for convenience of explanation. FIG. 5 is an enlarged view of a part of FIG. 4.

As illustrated in FIGS. 2 to 5, the sealed unit 51 includes a casing unit 512 in which the above-mentioned image sensor 511 and the like are housed, and an optical element 513.

The casing unit 512 is a part constituting the exterior of the sealed unit 51, and is made of, for example, a metal material such as aluminum, an aluminum alloy, stainless steel, titanium, or a titanium alloy. The casing unit 512 includes an optical element holding unit 512a (FIGS. 3 to 5).

The optical element holding unit 512a is a part provided on the distal end side of the casing unit 512 and holding the optical element 513. As illustrated in FIGS. 3 to 5, the optical element holding unit 512a includes first and second cylinders 512b and 512c and a connector 512d.

The first cylinder 512b is formed in a cylindrical shape and located on the distal end side.

The inside of the first cylinder 512b corresponds to an aperture 512e (FIGS. 4 and 5) according to the present disclosure. Then, the subject image emitted from the eyepiece unit 22 of the endoscope 2 is introduced into the casing unit 512 through the aperture 512e. Here, the inner circumferential surface of the aperture 512e is provided with a recess 512f (FIGS. 4 and 5) that is recessed from the distal end toward the proximal end side.

Furthermore, although a specific illustration is omitted, a screw groove is provided on the outer circumferential surface of the first cylinder 512b.

The second cylinder 512c is formed in a cylindrical shape having an internal size larger than the outer size of the first cylinder 512b, and located on the proximal end side.

The connector 512d is an annular plate body. The connector 512d is located between the first and the second cylinders 512b and 512c, and connects the first and the second cylinders 512b and 512c to each other.

The first and the second cylinders 512b and 512c and the connector 512d are integrally formed so that their central axes coincide with each other. In the following, the central axes will be referred to as a central axis Ax1 (FIG. 4).

The optical element 513 is a disk made of a translucent material such as sapphire glass, and having a pair of opposite plate surfaces that are parallel to each other and flat. Furthermore, although a specific illustration is omitted, a metal layer that may be brazed is provided (metallized) on the outer circumferential surface of the optical element 513. As illustrated in FIG. 4 or 5, the optical element 513 is disposed in the recess 512f, and fixed to the inner circumferential surface of the aperture 512e by brazing using solder SO in a posture in which a pair of plate surfaces are inclined with respect to a virtual plane orthogonal to the optical axis Ax. The casing unit 512 is thus airtightly sealed.

Here, in the optical element 513, the plate surface on the distal end side serves as an outer surface 513a (FIGS. 4 and 5) facing the space outside the casing unit 512. The plate surface on the proximal end side serves as an inner surface 513b (FIGS. 4 and 5) facing the space inside the casing unit 512.

In the first embodiment, as illustrated in FIGS. 2 to 5, the camera head 5 includes a watertight sealing member 53 that watertightly seals the solder SO joining the casing unit 512 and the optical element 513.

The detailed configuration of the watertight sealing member 53 will be described in "Configuration of Watertight Sealing Member" described below.

Here, although the specific illustration is omitted, the casing unit 512 is provided with an opening for outputting an image signal or the like from the image sensor 511 to the outside of the casing unit 512. Then, a hermetic connector is fixed to the inner circumferential surface of the opening by welding or the like. That is, the casing unit 512 is airtightly sealed by the optical element 513 and the hermetic connector.

Shape of Eyepiece Unit

Next, the shape of the eyepiece unit 22 will be described with reference to FIGS. 4 and 5.

The eyepiece unit 22 has a substantially cylindrical shape. In the following, the central axis of the eyepiece unit 22 will be referred to as a central axis Ax2 (FIG. 4). The central axis Ax2 coincides with the optical axis Ax.

In the eyepiece unit 22, an end face 221 on the proximal end side is a flat surface orthogonal to the central axis Ax2 (optical axis Ax).

Furthermore, in the eyepiece unit 22, the distal end side of the outer circumferential surface has a tapered shape with a diameter decreasing toward the distal end side. Hereinafter, the outer circumferential surface on the distal end side will be referred to as an inclined surface 222.

Configuration of Endoscope Connector

Next, the configuration of the endoscope connector 52 will be described with reference to FIGS. 2 to 5.

As illustrated in FIGS. 2 to 5, the endoscope connector 52 includes a mounting portion 521, an operation ring 522, and a plurality of locking members 523 (FIGS. 2 to 4).

The mounting portion 521 has a substantially cylindrical shape. In the following, the central axis of the mounting portion 521 will be referred to as a central axis Ax3 (FIG. 4). In the state where the endoscope connector 52 is fixed to the sealed unit 51, the central axes Ax1 and Ax3 coincide with each other. Here, the endoscope connector 52 is fixed to the sealed unit 51 by the watertight sealing member 53. The method of fixing the endoscope connector 52 will be described in "Method of Fixing Endoscope Connector and Watertight Sealing Member to Sealed Unit" described below.

As illustrated in FIGS. 2 to 5, the mounting portion 521 is provided with mounting recesses 521a that are recessed toward the proximal end side on the end face on the distal end side. The mounting recesses 521a are each a hole into which the eyepiece unit 22 fits when the camera head 5 is connected to the eyepiece unit 22. Hereinafter, the bottom surface of the mounting recesses 521a will be referred to as a bottom surface 521b (FIGS. 2 to 5), and the side surface of the mounting recesses 521a will be referred to as a side surface 521c (FIGS. 2 to 5).

The bottom surface 521b has a circular shape whose center coincides with the central axis Ax3. Furthermore, the side surface 521c has an annular shape whose center coincides with the central axis Ax3.

Furthermore, as illustrated in FIGS. 2 to 5, the mounting portion 521 is provided with a plurality of protrusions 521d that project from the side surface 521c toward the central axis Ax3.

The plurality of protrusions 521d are provided at positions that are rotationally symmetric with respect to the central axis Ax3. The surface on the distal end side of each of the plurality of protrusions 521d is a flat surface orthogonal to the central axis Ax3, and is a surface on which the end face 221 on the proximal end side of the eyepiece unit 22 abuts when the eyepiece unit 22 is fitted into the mounting recesses 521a. In the state where the eyepiece unit 22 is fitted into the mounting recesses 521a, the central axes Ax1 to Ax3 coincide with each other as illustrated in FIG. 4. That is, the surface on the distal end side of each of the plurality of protrusions 521d functions as a positioning surface for the camera head 5 with respect to the endoscope 2 (a positioning surface in the optical axis Ax direction, and a positioning surface in the rotation direction around each of the two axes orthogonal to the optical axis Ax).

Furthermore, as illustrated in FIGS. 3 to 5, the mounting portion 521 is provided with a connection hole 521e that is a circular hole penetrating from the end face on the proximal end side to the bottom surface 521b and having center coinciding with the central axis Ax3. The connection hole 521e is a hole through which the first cylinder 512b is inserted.

Furthermore, as illustrated in FIG. 4, the mounting portion 521 is provided with a plurality of through holes 521f penetrating from the outer circumferential surface into the mounting recesses 521a. The plurality of through holes 521f are provided at positions that are rotationally symmetric with respect to the central axis Ax3, respectively.

The operation ring 522 has an annular shape whose center coincides with the central axis Ax3, as illustrated in FIGS. 2 and 3. Then, the operation ring 522 faces the outer circumferential surface of the mounting portion 521 and is rotatably mounted on the mounting portion 521 about the central axis Ax3.

As illustrated in FIGS. 2 to 4, the plurality of locking members 523 are respectively arranged in the plurality of through holes 521f. The plurality of locking members 523 may be projected into and retracted out of the mounting recesses 521a through the plurality of through holes 521f in accordance with the rotation of the operation ring 522.

To connect the camera head 5 to the endoscope 2 (eyepiece unit 22), the operator fits the eyepiece unit 22 into the mounting recesses 521a and then rotates the operation ring 522 in a first direction. As a result, the plurality of locking members 523 each project into the mounting recesses 521a, and abut on the inclined surface 222 of the eyepiece unit 22. That is, the fitted state is locked.

On the other hand, to remove the camera head 5 from the endoscope 2, the operator rotates the operation ring 522 in a second direction opposite to the first direction. As a result, the plurality of locking members 523 may be moved out of the mounting recesses 521a. That is, the lock state described above is released.

Configuration of Watertight Sealing Member

Next, the configuration of the watertight sealing member 53 will be described with reference to FIGS. 2 to 5.

As illustrated in FIGS. 2 to 5, the watertight sealing member 53 includes an elastic portion 54 and a pressing portion 55.

The elastic portion 54 is made of an elastic material and has an annular shape as illustrated in FIG. 3.

Examples of the elastic material include silicone rubber and Teflon (registered trademark) rubber.

Here, in the elastic portion 54, the surface on the proximal end side serves as an abutting surface 541 (FIGS. 3 to 5) that abuts on the outer surface 513a of the optical element 513. On the other hand, the surface on the distal end side serves as a pressed surface 542 (FIGS. 3 to 5) pressed by the pressing portion 55.

In the first embodiment, the abutting surface 541 and the pressed surface 542 are each formed flat and are not parallel to each other. That is, the elastic portion 54 has a wedge shape.

The pressing portion 55 is a part that presses the elastic portion 54 toward the optical element 513. As illustrated in FIGS. 4 and 5, the pressing portion 55 includes a fixing portion 56 and a pressing portion body 57.

The fixing portion 56 is an annular plate body whose inner diameter dimension is substantially the same as or slightly larger than the outer diameter dimension of the first cylinder 512b. Although a specific illustration is omitted, the inner circumferential surface of the fixing portion 56 is provided with a screw groove for screwing into the screw groove provided on the outer circumferential surface of the first cylinder 512b.

As illustrated in FIGS. 4 and 5, the pressing portion body 57 includes first and second protrusions 571, 572.

The first protrusion 571 is an annular plate body that protrudes from the distal end side of the inner circumferential surface of the fixing portion 56 toward the central axis of the fixing portion 56.

The second protrusion 572 has a cylindrical shape that extends while bending at a right angle with respect to the first protrusion 571 from the inner edge of the first protrusion 571 toward the proximal end side. The end face of the second protrusion 572 on the proximal end side has an annular shape and corresponds to a pressing surface 573 (FIGS. 4 and 5) according to the present disclosure.

In the first embodiment, the pressing surface 573 is formed in a flat shape orthogonal to the central axis of the pressing portion 55 (the central axis Ax1 in the case where the watertight sealing member 53 is fixed to the sealed unit 51).

Method of Fixing Endoscope Connector and Watertight Sealing Member to Sealed Unit Next, a method of fixing the endoscope connector 52 and the watertight sealing member 53 to the sealed unit 51 will be described.

First, the operator inserts the first cylinder 512b into the connection hole 521e.

Next, the operator holds the elastic portion 54 against the outer surface 513a of the optical element 513. In this state, the abutting surface 541 is inclined with respect to the virtual plane orthogonal to the central axis Ax1 (optical axis Ax) following the outer surface 513a. On the other hand, the pressed surface 542 is parallel to the virtual plane.

Next, the operator rotates the pressing portion 55 while inserting the distal end side of the first cylinder 512b into the fixing portion 56, and causes the screw groove provided on the inner circumferential surface of the fixing portion 56 to screw into the screw groove provided on the outer circumferential surface of the first cylinder 512b. As a result, the pressing portion 55 gradually moves to the proximal end side, whereby the pressing surface 573 presses the elastic portion 54 toward the optical element 513.

Through the operation described above, the watertight sealing member 53 is fixed to the sealed unit 51.

In this state, the inner edge of the annular elastic portion 54 is located closer to the central axis Ax1 side than the annular solder SO between the casing unit 512 and the optical element 513 is when viewed from the direction along the central axis Ax1 (FIG. 4, FIG. 5). That is, the solder SO is watertightly sealed by the watertight sealing member 53.

Furthermore, in this state, the surface on the proximal end side of the fixing portion 56 in the pressing portion 55 presses the bottom surface 521b toward the proximal end side, whereby the endoscope connector 52 (mounting portion 521) is clamped between the pressing portion 55 and the connector 512d. That is, the pressing portion 55 also has a function of fixing the endoscope connector 52 to the sealed unit 51. Note that, annular elastic members R1 and R2 (FIGS. 4 and 5) are provided between the pressing portion 55 and the mounting portion 521 and between the mounting portion 521 and the optical element holding unit 512a in order to ensure watertightness. Note that, as the annular elastic members R1 and R2, for example, O-rings made of an elastic resin is used. In addition, it suffices if the elastic members R1 and R2 have a structure and a material that may ensure watertightness between the pressing portion 55 and the mounting portion 521 and between the mounting portion 521 and the optical element holding unit 512a, and they are not limited to O-rings made of an elastic resin.

The first embodiment described above provides the following effects.

The camera head 5 according to the first embodiment includes the above-described watertight sealing member 53 watertightly sealing the annular solder SO between the casing unit 512 and the optical element 513.

Thus, even when the surface roughness of the surface of the solder SO becomes rough, the solder SO is watertightly sealed by the watertight sealing member 53, so that no dirt will remain on this surface while the camera head 5 is being used.

The camera head 5 according to the first embodiment thus requires no attention to the surface of the solder SO in autoclave treatment, and disinfection treatment by wiping or immersion, and the cleanability may be improved.

In addition, the pressing portion 55 included in the watertight sealing member 53 has a function of fixing the endoscope connector 52 to the sealed unit 51. Therefore, it is not necessary to separately provide a member for fixing the endoscope connector 52 to the sealed unit 51, and the number of parts of the camera head 5 may be reduced.

Furthermore, the elastic portion 54 included in the watertight sealing member 53 has a wedge shape in which the abutting surface 541 and the pressed surface 542 are not parallel to each other. Therefore, the elastic portion 54 is installed in a posture in which the pressed surface 542 is parallel to the virtual plane orthogonal to the optical axis Ax, whereby the pressing surface 573 parallel to the virtual plane presses the elastic portion 54 toward the optical element 513. That is, the elastic portion 54 (pressed surface 542) may be pressed substantially evenly by the pressing surface 573.

Second Embodiment

Next, a second embodiment will be described.

In the following description, the same reference numerals are given to components that are the same as those in the first embodiment described above, and detailed description thereof will be omitted or simplified.

Figure 6:
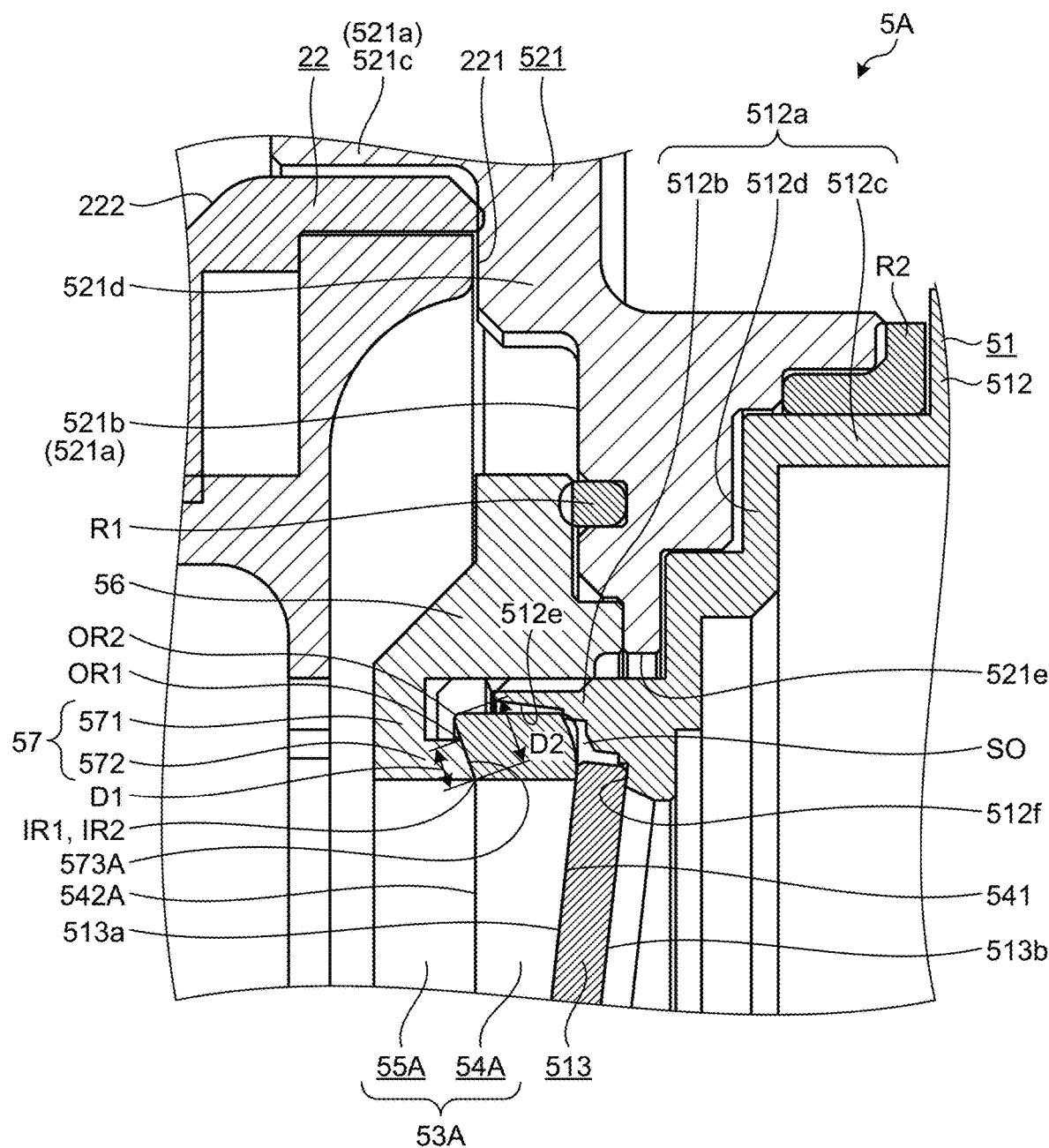
FIG. 6 is a diagram illustrating a watertight sealing member according to a second embodiment.

FIG. 6 is a diagram illustrating a watertight sealing member 53A according to the second embodiment. Specifically, FIG. 6 is a cross-sectional view corresponding to FIG. 5.

A camera head 5A according to the second embodiment, as illustrated in FIG. 6, differs from the camera head 5 described in the above-described first embodiment in that the watertight sealing member 53A is provided instead of the watertight sealing member 53. The watertight sealing member 53A includes an elastic portion 54A and a pressing portion 55A having different shapes from the elastic portion 54 and the pressing portion 55, respectively.

As illustrated in FIG. 6, the pressing portion 55A has a pressing surface 573A having a shape different from that of the pressing surface 573 of the pressing portion 55 in the first embodiment described above.

The annular pressing surface 573A is inclined such that an inner edge IR1 of the annular shape is located closer to the proximal end side than an outer edge OR1 is. In the second embodiment, the inner edge IR1 and the outer edge OR1 in the pressing surface 573A are connected by a straight line when viewed in the cross section as illustrated in FIG. 6. That is, the pressing surface 573A is formed so as to constitute a side surface of a truncated cone.

As illustrated in FIG. 6, the elastic portion 54A has a pressed surface 542A having a shape different from that of the pressed surface 542 of the elastic portion 54 in the first embodiment described above.

The annular pressed surface 542A is inclined following the pressing surface 573A. That is, the annular pressed surface 542A is inclined such that an inner edge IR2 of the annular shape is located closer to the proximal end side than an outer edge OR2 is.

Furthermore, a length dimension D2 between the inner edge IR2 and the outer edge OR2 of the pressed surface 542A is set to be larger than a length dimension D1 between the inner edge IR1 and the outer edge OR1 of the pressing surface 573A. That is, the wall thickness of the elastic portion 54A in the radial direction is set to be larger than the length dimension D1 of the pressing surface 573A. With the watertight sealing member 53A fixed to the sealed unit 51, the inner edges IR1 and IR2 are located at positions substantially coinciding with each other, and the outer edge OR2 is located farther away from the central axis Ax1 than the outer edge OR1 is.

According to the second embodiment described above, in addition to the same effects as those of the first embodiment described above, the following effects are obtained.

Incidentally, in the autoclave treatment, after the camera head 5A is placed in a high-temperature and high-pressure steam sterilizer, the inside of the high-temperature and high-pressure steam sterilizer needs to be evacuated in some cases. In this case, the elastic portion 54A is pulled from between the pressing surface 573A and the outer surface 513a of the optical element 513 toward the central axis Ax3, which may fail to ensure sufficient watertightness.

The pressing surface 573A according to the second embodiment is inclined such that the inner edge IR1 is located closer to the proximal end side than the outer edge OR1 is. Thus, the elastic portion 54A is not easily pulled toward the central axis Ax3 by the pressing surface 573A, and the watertight state may be maintained even when the above-mentioned evacuation is performed.

In particular, the length dimension D2 of the pressed surface 542A is set to be larger than the length dimension D1 of the pressing surface 573A. With the watertight sealing member 53A fixed to the sealed unit 51, the inner edges IR1 and IR2 are located at positions substantially coinciding with each other, and the outer edge OR2 is located farther away from the central axis Ax1 than the outer edge OR1 is. For this reason, the part in the elastic portion 54A located outside the outer edge OR1 away from the central axis Ax1 is difficult to enter between the pressing surface 573A and the outer surface 513a of the optical element 513, which may make the structure of the elastic portion 54A more difficult to pull toward the central axis Ax3. That is, even when the above-mentioned evacuation is performed, the watertight state may be sufficiently maintained.

The pressed surface 542A is inclined following the pressing surface 573A. Thus, the elastic portion 54A (pressed surface 542A) may be pressed substantially evenly by the pressing surface 573A.

Third Embodiment

Next, a third embodiment will be described.

In the following description, the same reference numerals are given to components that are the same as those in the first embodiment described above, and detailed description thereof will be omitted or simplified.

Figure 7:
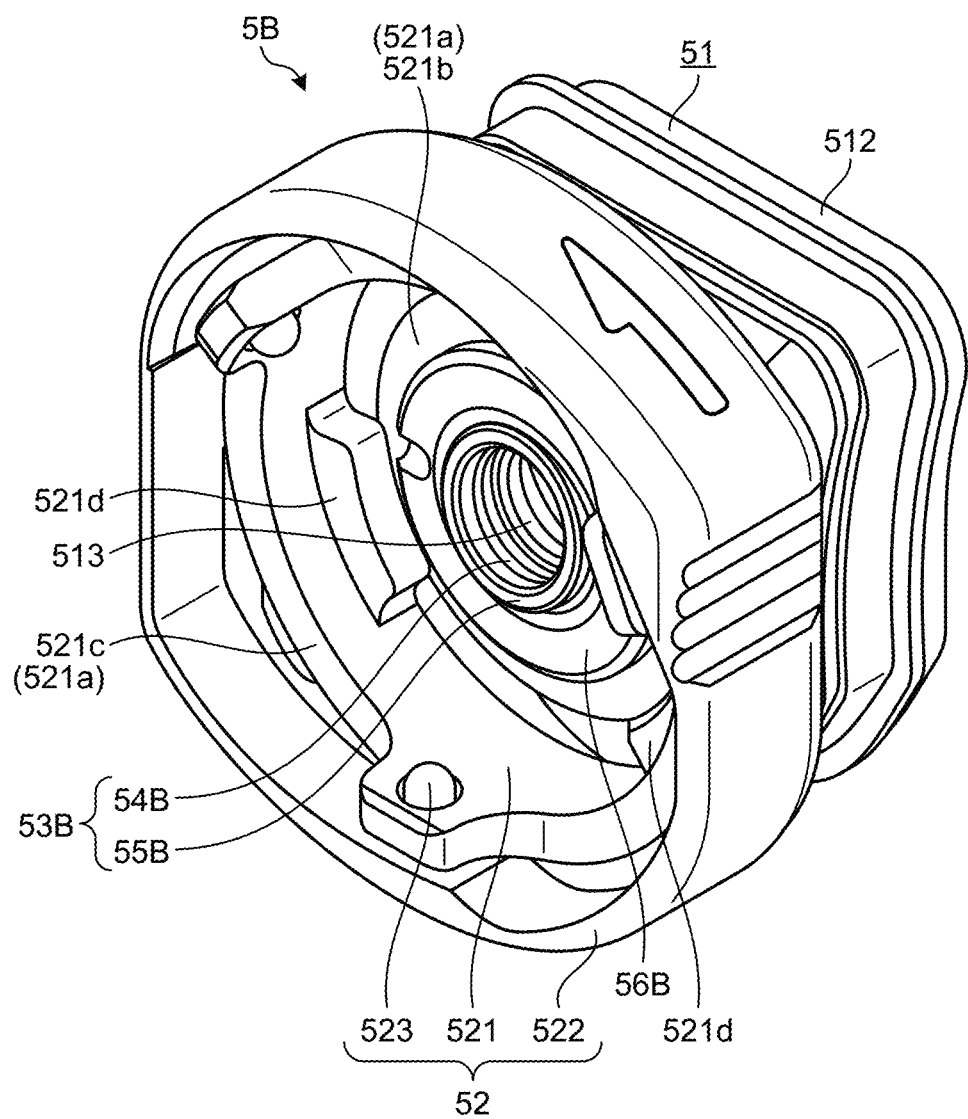
FIG. 7 is a diagram illustrating a configuration of a camera head according to a third embodiment.
Figure 8:
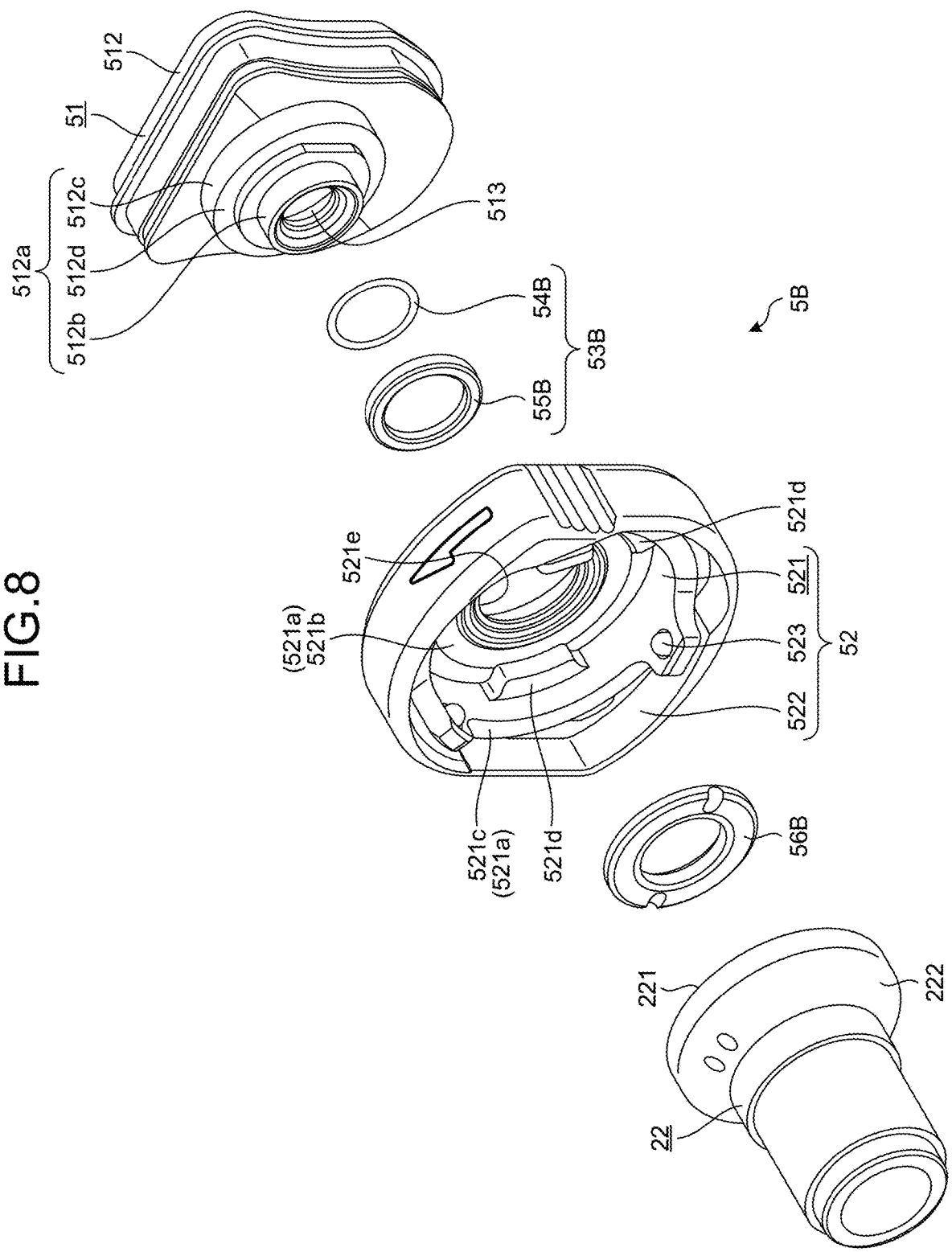
FIG. 8 is a diagram illustrating the configuration of the camera head according to the third embodiment.
Figure 9:
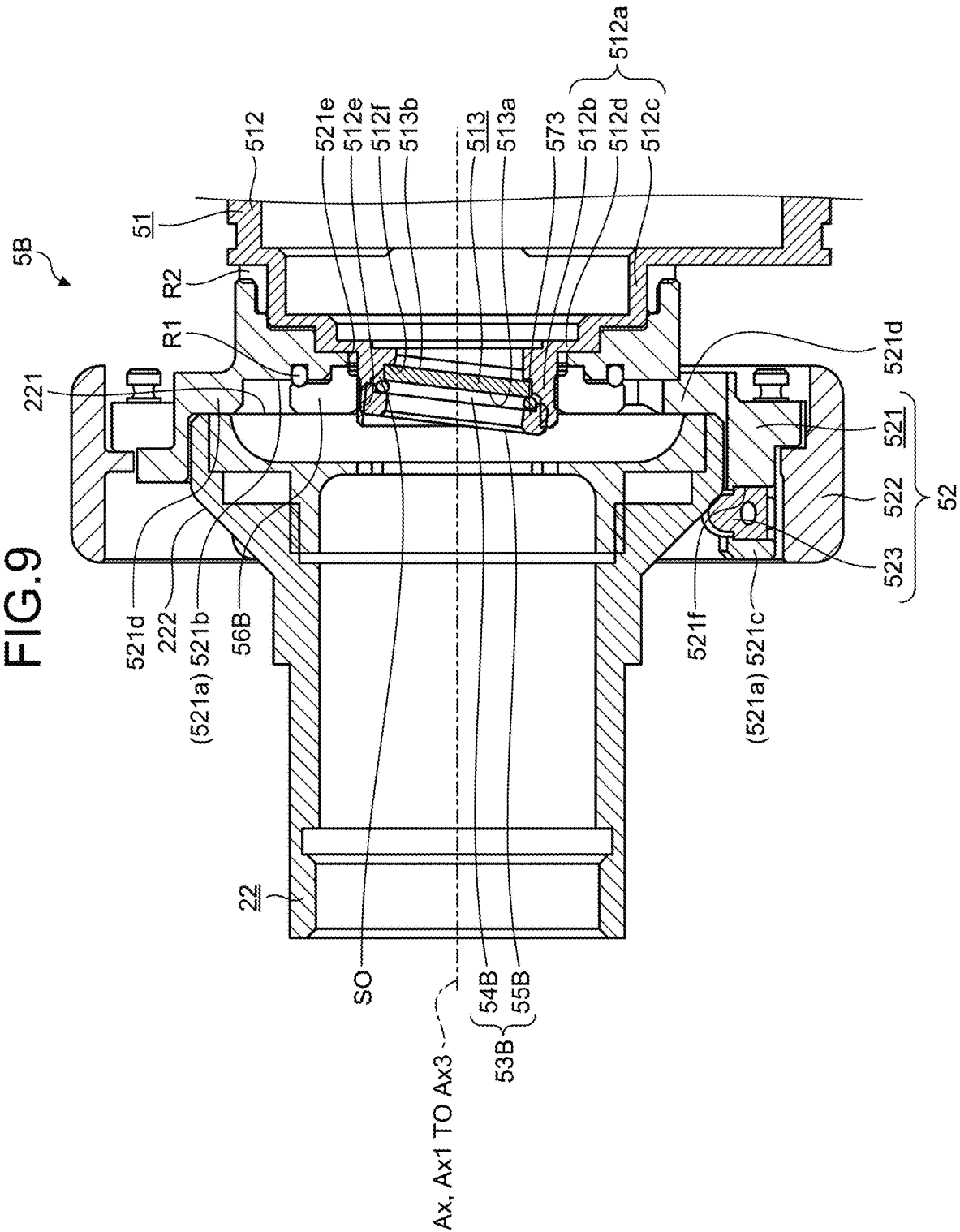
FIG. 9 is a diagram illustrating the configuration of the camera head according to the third embodiment.
Figure 10:
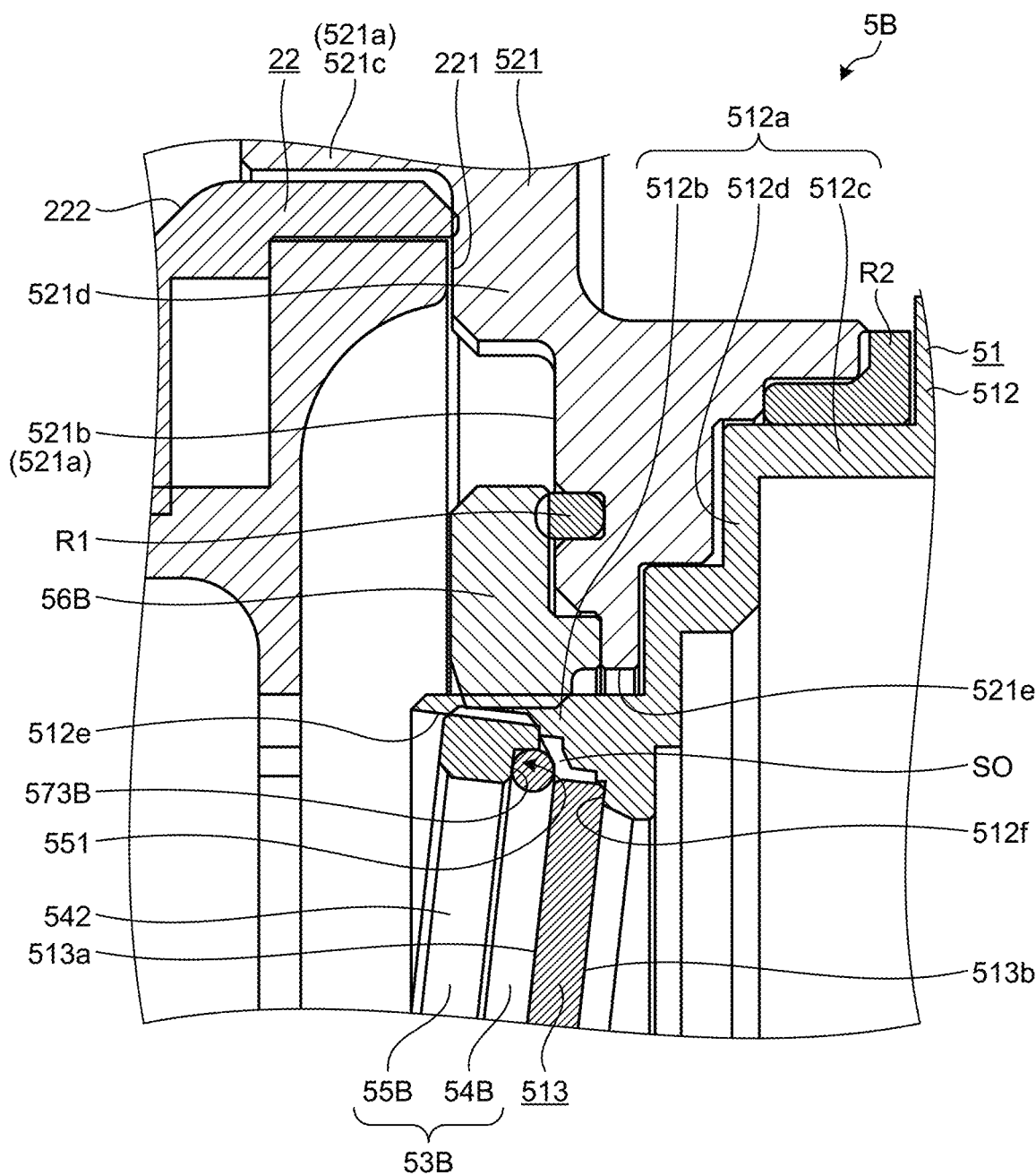
FIG. 10 is an enlarged view of a part of FIG. 9.

FIGS. 7 to 9 are diagrams illustrating the configuration of a camera head 5B according to the third embodiment. Specifically, FIGS. 7 to 9 are diagrams corresponding to FIGS. 2 to 4, respectively. FIG. 10 is a diagram corresponding to FIG. 5, and an enlarged view of a part of FIG. 9.

In the first embodiment described above, the pressing portion 55 has a function of fixing the endoscope connector 52 to the sealed unit 51.

By contrast, a watertight sealing member 53B included in the camera head 5B according to the third embodiment does not have a function of fixing the endoscope connector 52 to the sealed unit 51.

In the third embodiment, as illustrated in FIGS. 7 to 10, the camera head 5B includes a fixing portion 56B having substantially the same shape and same function as the fixing portion 56 in the first embodiment described above, besides watertight sealing member 53B. That is, the endoscope connector 52 is fixed to the sealed unit 51 by the fixing portion 56B.

Furthermore, in the third embodiment, although specific illustration is omitted, the inner circumferential surface of the first cylinder 512b is provided with a screw groove so as to draw a spiral around the normal direction of the outer surface 513a of the optical element 513.

As illustrated in FIGS. 7 to 10, the watertight sealing member 53B includes an elastic portion 54B and a pressing portion 55B having different shapes from the elastic portion 54 and the pressing portion 55, respectively, in the first embodiment described above.

The elastic portion 54B has an annular shape and is composed of a general O-ring having a circular cross section.

The pressing portion 55B is an annular plate body whose outer diameter dimension is substantially the same as or slightly smaller than the inner diameter dimension of the first cylinder 512b. Although a specific illustration is omitted, the outer circumferential surface of the pressing portion 55B is provided with a screw groove for screwing into a screw groove provided on the inner circumferential surface of the first cylinder 512b.

As illustrated in FIG. 10, the pressing portion 55B is provided with a pressing recess 551 that is recessed toward the distal end side on the surface on the proximal end side. The bottom surface of the pressing recess 551 corresponds to a pressing surface 573B according to the present disclosure.

The method of fixing the watertight sealing member 53B to the sealed unit 51 is as follows.

First, the operator holds the elastic portion 54B against the outer surface 513a of the optical element 513.

Next, the operator rotates the pressing portion 55B while inserting the pressing portion 55B into the first cylinder 512b from the distal end side of the first cylinder 512b, and causes the screw groove provided on the outer circumferential surface of the pressing portion 55B to screw into the screw groove provided on the inner circumferential surface of the first cylinder 512b. As a result, the pressing portion 55B gradually moves toward the proximal end side along the normal direction of the outer surface 513a of the optical element 513, and the pressing surface 573B presses the elastic portion 54B toward the optical element 513.

Through the operation described above, the watertight sealing member 53B is fixed to the sealed unit 51.

In this state, the inner edge of the annular elastic portion 54B is located closer to the central axis Ax1 side than the annular solder SO between the casing unit 512 and the optical element 513 is when viewed from the direction along the central axis Ax1 (FIG. 9, FIG. 10). That is, the solder SO is watertightly sealed by the watertight sealing member 53B.

According to the third embodiment described above, in addition to the same effects as those of the first embodiment described above, the following effects are obtained.

In the camera head 5B according to the third embodiment, the fixing portion 56B for fixing the endoscope connector 52 is provided, besides the watertight sealing member 53B.

In this manner, as the screwing structure between the pressing portion 55B and the first cylinder 512b, a structure provided with a screw groove so as to draw a spiral about the normal direction of the outer surface 513a of the optical element 513 may be adopted. Therefore, a general O-ring having an annular shape and a circular cross section may be adopted as the elastic portion 54B, which makes it unnecessary to manufacture a dedicated elastic portion of a wedge shape or the like.

Other Embodiments

The modes for carrying out the present disclosure have been described above, but the present disclosure should not be limited only by the first to the third embodiments described above.

In the first to the third embodiments described above, the casing unit 512 is not limited to one composed of a single member, and may be configured by combining a plurality of members. Furthermore, the casing unit 512 is not limited to a metal material, and may be made of ceramic. In this case, it is necessary to provide a metal layer on the inner circumferential surface of the aperture 512e in order to enable brazing with solder.

In the second embodiment described above, the annular pressing surface 573A may have any other shape as long as the inner edge IR1 of the annular shape is inclined so as to be located closer to the proximal end side than the outer edge OR1 is. For example, when viewed in the cross section illustrated in FIG. 6, the pressing surface may be configured such that the inner edge IR1 and the outer edge OR1 of the annular shape are connected by a curved line.

While the pressed surface 542A is inclined following the pressing surface 573A in the second embodiment described above, this is not limiting, and the same shape as that in the first embodiment may be used.

In the second embodiment described above, the length dimensions D1 and D2 may be the same.

With the camera head according to the present disclosure, the cleanability may be improved.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A camera head comprising:
   a casing including an opening and configured to receive a subject image introduced inside through the opening;
   an image sensor housed in the casing and configured to capture the subject image;
   an optical element made of a translucent material and fixed to an inner circumferential surface of the opening by brazing with solder to airtightly seal inside of the casing, wherein an outer surface of the optical element opposite the opening of the casing are exposed; and
   a watertight sealing member fixed to the casing and watertightly sealing the solder joining the casing and the optical element, the watertight sealing member including
      an annular elastic portion made of an elastic material, and
      a pressing portion including an annular pressing surface configured to press the annular elastic portion toward the optical element and the solder when the annular elastic portion directly abuts the outer surface of the optical element and the solder, the pressing portion being fixed to the casing, wherein
   the solder is between the casing and the annular elastic portion,
   the casing includes an extension portion that extends towards the pressing portion along the annular elastic portion and the solder, and
   the pressing portion includes a protrusion that extends towards and contacts the annular elastic portion and overlaps the extension portion.

2. The camera head according to claim 1, further comprising
   an endoscope connector detachably connected to an eyepiece of an endoscope, wherein
   the pressing portion is fixed to the casing to press the annular elastic portion toward the optical element, and the endoscope connector is fixed to the casing.

3. The camera head according to claim 1, further comprising:
   an endoscope connector detachably connected to an eyepiece of an endoscope; and
   a fixing portion configured to fix the endoscope connector to the casing.

4. The camera head according to claim 1, wherein
   the optical element is formed of a plate such that the outer surface of the optical element and an inner surface of the optical element facing a space inside the casing are parallel to each other, wherein the optical element is fixed to the inner circumferential surface of the opening in a posture in which the outer surface and the inner surface are inclined with respect to a virtual plane orthogonal to an optical axis of the subject image, and the annular elastic portion includes
an abutting surface directly abutting the outer surface of the optical element, the abutting surface being inclined with respect to the virtual plane to be parallel to the outer surface of the optical element, and
a pressed surface opposite the abutting surface, the pressed surface being not parallel to the abutting surface and being pressed by the pressing surface.

5. The camera head according to claim 1, wherein the pressing surface is inclined such that an inner edge of an annular shape of the pressing surface is closer to the optical element than an outer edge of the annular shape of the pressing surface.

6. The camera head according to claim 5, wherein
the annular elastic portion includes a pressed surface pressed against the pressing surface, the pressing surface having an annular shape, and
a distance between an inner edge and an outer edge of the annular shape of the pressed surface is larger than a distance between the inner edge and the outer edge of the annular shape of the pressing surface.

7. The camera head according to claim 5, wherein
the annular elastic portion includes a pressed surface pressed against the pressing surface, and
the pressed surface is parallel to the pressing surface.

8. The camera head according to claim 1, wherein the pressing surface is flat orthogonal to a central axis of the camera head.

9. The camera head according to claim 1, wherein the annular elastic portion has a circular cross section and the pressing surface includes a pressing recess pressing the circular cross section.

10. The camera head according to claim 9, wherein the annular elastic portion partially covers the solder and the pressing portion extending toward the optical element from the pressing recess together with the annular elastic portion completely cover the solder.

11. The camera head according to claim 1, wherein the annular elastic portion completely covers the solder.

12. The camera head according to claim 1, wherein the annular elastic portion partially covers the solder and the annular elastic portion and the pressing portion together completely cover the solder.

13. The camera head according to claim 1, wherein the subject image is incident on the outer surface of the optical element.

14. A connector between a casing including an opening and configured to receive a subject image introduced inside through the opening and an image sensor housed in the casing and configured to capture the subject image, the casing having an optical element made of a translucent material and fixed to an inner circumferential surface of the opening by brazing with solder to airtightly seal inside of the casing, and an eyepiece of a scope, the connector comprising:
a mount to receive the optical element in the casing and the eyepiece; and
a watertight sealing member within the mount and watertightly sealing the solder joining the casing and the optical element, the watertight sealing member including
an annular elastic portion made of an elastic material, and
a pressing portion including an annular pressing surface configured to press the annular elastic portion toward the optical element and the solder when the annular elastic portion directly abuts an outer surface of the optical element and the solder, the pressing portion being fixed to the casing, wherein
the solder is between the casing and the annular elastic portion,
the casing includes an extension portion that extends towards the pressing portion along the annular elastic portion and the solder, and
the pressing portion includes a protrusion that extends towards and contacts the annular elastic portion and overlaps the extension portion.

15. The connector according to claim 14, wherein the pressing portion is configured to fix the mount to the casing.

16. The connector according to claim 14, wherein the annular elastic portion completely covers the solder when connected to the casing.

17. The connector according to claim 14, wherein the annular elastic portion partially covers the solder and the annular elastic portion and the pressing portion together completely cover the solder when connected to the casing.

18. The connector according to claim 14, wherein the pressing surface is inclined such that an inner edge of an annular shape of the pressing surface is closer to the optical element than an outer edge of the annular shape of the pressing surface.

19. The connector according to claim 14, further comprising a fixing portion configured to fix the mount to the casing.

20. The connector according to claim 14, wherein the subject image is incident on the outer surface of the optical element.

* * * * *